United States Patent [19]

Packman

[11] 4,370,325
[45] Jan. 25, 1983

[54] PHARMACEUTICAL COMPOSITIONS AND METHOD OF TREATMENT

[75] Inventor: Albert M. Packman, Dresher, Pa.

[73] Assignee: Dermik Laboratories, Fort Washington, Pa.

[21] Appl. No.: 25,388

[22] Filed: Mar. 30, 1979

[51] Int. Cl.³ .............................................. A61K 31/555
[52] U.S. Cl. ...................................... 424/245; 424/70; 424/180; 424/362
[58] Field of Search ................. 424/263, 245; 546/290

[56] References Cited

U.S. PATENT DOCUMENTS

| | | | |
|---|---|---|---|
| 2,686,786 | 8/1954 | Shaw et al. | 546/290 |
| 2,742,393 | 4/1956 | Bernstein et al. | 546/290 |
| 2,742,476 | 4/1956 | Bernstein et al. | 546/261 |
| 2,809,971 | 10/1957 | Bernstein et al. | 546/290 |
| 3,027,371 | 3/1962 | Starrs | 424/245 X |
| 3,027,372 | 3/1962 | Starrs | 424/245 X |
| 3,235,455 | 2/1966 | Judge et al. | 260/270 K |
| 3,269,904 | 8/1966 | Bernstein et al. | 546/290 |
| 3,346,578 | 10/1967 | Langlykke et al. | 424/263 X |
| 3,583,999 | 6/1971 | Damico | 546/290 |
| 3,767,788 | 10/1973 | Rankin | 424/78 |
| 3,890,434 | 6/1975 | Weisse et al. | 424/245 |
| 4,142,985 | 3/1979 | Louderback et al. | 424/361 |
| 4,152,430 | 5/1979 | Klein et al. | 424/263 |
| 4,152,431 | 5/1979 | Klein | 424/263 |

*Primary Examiner*—Dale R. Ore
*Attorney, Agent, or Firm*—James A. Nicholson; Austin R. Miller; John Lezdey

[57] ABSTRACT

The present invention relates to novel ophthalmic and/or otic compositions and to a method of treating eye and ear irritations and inflammation in warm blooded animals by administering to a warm blooded animal in need of such treatment an effective amount of bis-(2-pyridyl-1-oxide) disulfide and/or at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2.

18 Claims, No Drawings

PHARMACEUTICAL COMPOSITIONS AND METHOD OF TREATMENT

BACKGROUND OF THE INVENTION

The present invention relates to the novel method of treating ear and eye irritations and inflammation in mammals by administering bis-(2-pyridyl-1-oxide) disulfide and/or at least one metal salt of bis-(2-pyridyl-1-oxide) disulfide and to novel compositions containing such compounds.

More particularly, the present invention relates to ophthalmic and/or otic solutions which are suitable for general use in the eyes and ears of humans and domestic animals with various eye and/or ear irritation disorders. The ophthalmic and otic solutions of the present invention are useful in the treatment of anti-bacterial and/or anti-fungal irritation disorders which occur from swimming such as conjunctivitis and "swimmer's ear". The ophthalmic solution is also useful as a lubricating and soothing agent for the eye after traumatic injury or surgery. It may also be used as a corneal wetting solution for use with contact lens and for treatment of dry eye syndrome.

Bis-(2-pyridyl-1-oxide) disulfide (also referred to as 2,2'-dithiodipyridine-1-1'-dioxide) and various derivatives thereof, have previously been disclosed in the literature. For example, U.S. Pat. No. 2,742,476 discloses bis-(2-pyridyl-1-oxide) disulfide and the lower alkyl substituted derivatives thereof. U.S. Pat. No. 3,027,371 discloses molybdate derivatives, U.S. Pat. No. 3,027,732 discloses stannous chloride derivatives, and U.S. Pat. No. 3,346,578 discloses stannous fluoride derivatives of bis-(2-pyridyl-1-oxide) disulfide and each refer to the anti-fungal and the anti-bacterial properties of said derivatives.

U.S. Pat. No. 3,890,434 discloses hair and antiseptic formulations containing adducts of bis-(2-pyridyl-1-oxide) disulfide with alkaline earth metal salts. U.S. Pat. No. 3,767,788 discloses ophthalmic solutions containing polyethylene oxide and a biocide such as sodium ethylmercurithiosalicylate.

DETAILED DESCRIPTION OF THE INVENTION

Now it has been found that even more pronounced pharmacological properties for the relief and inhibition of ear and eye irritations and inflammation conditions can be provided by administration of a bis-(2-pyridyl-n-oxide) disulfide compound, that is, bis-(2-pyridyl-1-oxide) disulfide and/or the adducts of bis-(2-pyridyl-1-oxide) disulfide according to this invention. More specifically, these adducts have the formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2. More particularly, the anion Y is selected from the group consisting of halides, sulfates, nitrates, chlorates and acetates, with the chlorides and sulfates being most preferable. More particularly preferred are the water-soluble adducts, especially calcium chloride ($CaCl_2$) or magnesium sulfate ($MgSO_4$). Also included in the adducts of this invention are the hydrates of the aforementioned compounds, i.e., adducts including $nH_2O$ groups where n is an integer of 0 to 10. Additionally, the adducts (I) may contain one or more substituents on either or both pyridine ring structures such as alkyls, halogens and alkoxy groups. It is further noted that $(C_5H_4NOS)_2$ as used in (I) above and throughout the specification and claims represents bis-(2-pyridyl-1-oxide) disulfide and the structural formula shown as follows:

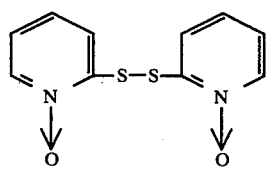

Among the adducts which may be utilized in this invention may be mentioned:

Bis-(2-pyridyl-1-oxide) disulfide magnesium sulfate, bis-(2-pyridyl-1-oxide) disulfide magnesium acetate, bis-(2-pyridyl-1-oxide) disulfide magnesium chloride, bis-(2-pyridyl-1-oxide) disulfide magnesium bromide, bis-(2-pyridyl-1-oxide) disulfide calcium chloride, bis-(2-pyridyl-1-oxide) disulfide calcium sulfate, bis-(2-pyridyl-1-oxide) disulfide calcium nitrate, bis-(2-pyridyl-1-oxide) disulfide calcium acetate, bis-(2-pyridyl-1-oxide) disulfide calcium chlorate, bis-(2-pyridyl-1-oxide) disulfide barium chloride, bis-(2-pyridyl-1-oxide) disulfide barium sulfate, bis-(2-pyridyl-1-oxide) disulfide barium nitrate, bis-(2-pyridyl-1-oxide) disulfide barium acetate, bis-(2-pyridyl-1-oxide) disulfide barium chlorate, bis-(2-pyridyl-1-oxide) disulfide strontium chloride, bis-(2-pyridyl-1-oxide) disulfide strontium sulfate, bis-(2-pyridyl-1-oxide) disulfide strontium nitrate, bis-(2-pyridyl-1-oxide) disulfide strontium acetate, bis-(2-pyridyl-1-oxide) disulfide strontium chlorate, bis-(2-pyridyl-1-oxide) disulfide potassium chloride, bis-(2-pyridyl-1-oxide) disulfide potassium sulfate, bis-(2-pyridyl-1-oxide) disulfide potassium nitrate, bis-(2-pyridyl-1-oxide) disulfide potassium acetate, bis-(2-pyridyl-1-oxide) disulfide potassium chlorate, bis-(2-pyridyl-1-oxide) disulfide sodium chloride, bis-(2-pyridyl-1-oxide) disulfide sodium sulfate, bis-(2-pyridyl-1-oxide) disulfide sodium nitrate, bis-(2-pyridyl-1-oxide) disulfide sodium acetate, bis-(2-pyridyl-1-oxide) disulfide sodium chlorate, bis-(2-pyridyl-1-oxide) disulfide zinc chloride, bis-(2-pyridyl-1-oxide) disulfide zinc sulfate, bis-(2-pyridyl-1-oxide) disulfide zinc nitrate, bis-(2-pyridyl-1-oxide) disulfide zinc acetate, bis-(2-pyridyl-1-oxide) disulfide zinc chlorate, bis-(2-pyridyl-1-oxide) disulfide stannous chloride, bis-(2-pyridyl-1-oxide) disulfide stannous sulfate, bis-(2-pyridyl-1-oxide) disulfide stannous nitrate, bis-(2-pyridyl-1-oxide) disulfide stannous acetate, bis-(2-pyridyl-1-oxide) disulfide stannous chlorate, bis-(2-pyridyl-1-oxide) disulfide zirconium chloride, bis-(2-pyridyl-1-oxide) disulfide zirconium sulfate, bis-(2-pyridyl-1-oxide) disulfide zirconium nitrate, bis-(2-pyridyl-1-oxide) disulfide zirconium acetate, bis-(2-pyridyl-1-oxide) disulfide zirconium chlorate, bis-(2-pyridyl-1-oxide) disulfide ferrous chloride, bis-(2-pyridyl-1-oxide) disulfide ferrous sulfate, bis-(2-pyridyl-1-oxide) disulfide ferrous nitrate, bis-(2-pyridyl-1-oxide) disulfide ferrous acetate, bis-(2-pyridyl-1-oxide) disulfide ferrous chlorate, bis-(2-pyridyl-1-oxide) disulfide lithium chloride, bis-(2-pyridyl-1-oxide) disulfide lithium sulfate, bis-(2-pyridyl-1-oxide) disulfide lithium nitrate, bis-(2-pyridyl-1-oxide) disulfide lithium acetate, and bis-(2-pyridyl-1-oxide) disulfide lithium chlorate.

In accordance with the present invention, it has been discovered that ophthalmic and/or otic solutions can be provided which are useful for the relief and inhibition of eye and/or ear irritation disorders resulting from a broad variety of organisms, i.e. Gram-positive organisms such as Staphylococcus aureus, Sarcina lutea, and Streptococcus pyogenes; Gram-negative organisms such as Escherichia coli and Pseudomonas aeruginosa, and Fungi (including yeasts and dermatophytes) such as: *Aspergillus niger, Mycrosporum gypseum,* and *Candida albicans.*

Accordingly, it is an object of the present invention to provide ophthalmic and/or otic solutions which are suitable for general use in the eye and/or ear of both humans and domestic animals.

Another object of the present invention provides ophthalmic and/or otic solutions which are useful in the treatment or inhibition of bacterial and/or fungal infections.

It is a further object of the present invention to provide ophthalmic and/or otic solutions which are useful in the treatment or inhibition of inflammatory conditions of the eye and/or ear.

Yet another object is to provide an ophthalmic solution which serves to alleviate minor irritations associated with the wearing of contact lenses or from contact with air pollutants.

These and other objects of the present invention will become more apparent from the following detailed description and the accompanying claims.

In general, the present invention is directed to ophthalmic and/or otic solutions which are aqueous solutions of a bis-(2-pyridyl-n-oxide) disulfide compound. Preferably, the ophthalmic solution also includes monovalent cation-containing salts at a level sufficient to make the solution isotonic. This solution may, in addition, contain benzalkonium chloride and various polymers and/or polysaccharides.

The otic solution of the present invention is an aqueous solution of bis-(2-pyridyl-1-oxide) disulfide compound. The otic solution may also contain a pharmacologically acceptable glycol such as polyethylene glycol and polypropylene glycol, polystyrene sulfonate, polyethylene oxide, and suitable polysaccharides.

The particular polysaccharides useful in the opthalmic and/or otic solution of the present invention are selected from dextrans and arabinogalactans. Especially useful dextrans are those having a molecular weight in the range of about 10,000 to about 1,000,000 and preferably from about 20,000 to about 200,000.

The arabinogalactans useful in the solutions of the present invention are those having a molecular weight in the range of 10,000 to 250,000 and are commercially available under the trade name, Stractan.

Benzalkonium chloride is the common name used to define monoalkyldimethylbenzylammonium chloride compounds of the general formula $[C_6H_5CH_2N(CH_3)_2R]^+Cl^-$ were R is a mixture of alkyl groups containing 8 to 18 carbon atoms. U.S.P. benzalkonium chloride contains a particular blend of alkyl radicals. As used herein, the term benzalkonium chloride is intended to include any benzyl quaternary ammonium compound containing one or two $C_8$–$C_{18}$ long chain alkyl radicals.

The incorporation of benzalkonium chloride in various ophthalmic solutions as a biocide is known.

The bis-(2-pyridyl-1-oxide) disulfide compound is present in the ophthalmic and/or otic solution at a level of from about 0.001% to about 5%, preferably from about 0.01% to about 2%.

Benzalkonium chloride is present in the ophthalmic solution at a level of from about 0.001% to about 0.1% by weight, preferably, from about 0.004% to to about 0.02% by weight.

The polysaccharides of the present invention are present in the ophthalmic and/or otic solutions at a level of from about 0.001% to about 5% by weight. At this level of use, the solutions generally have a viscosity in the range of from about 1 cps to about 25 cps at 25° C. The viscosity of the solutions are measured on a Wells-Brookfield Microviscometer (cone and plate) Model LVT. The solutions of the present invention do not exhibit any gel-like properties and the viscosity is low compared to other polymer-containing solutions. However, the viscosity can be adjusted within the indicated range by inclusion of water soluble viscosity building agents. Suitable viscosity building agents include natural gums, such as guar gum and gum tragacanth; gelatin; starch derivatives; polymeric glycols; and cellulosic polymers, such as hydroxyethylcellulose, hydroxypropylcellulose, methylcellulose, hydroxypropylmethylcellulose, and carboxymethylcellulose. Viscosity building agents, when used, are present in the solutions of the invention at a level of from about 0.001% to about 1.0% by weight. The exact percentage depends on the molecular weight of the polymer used which is within the skill of the art. When a viscosity building agent is utilized, the viscosity of the solution may be between about 1 cps and about 25 cps, preferably between about 3 cps and about 15 cps.

For most purposes, the benzalkonium chloride present in the ophthalmic solution provides the desired preservative effect. However, additional biocides may be incorporated, if desired. For example, it is generally desirable to incorporate a suitable chelating agent to enhance the preservative effect of the benzalkonium chloride. Suitable chelating agents include di-, tri-, or tetrasodium ethylene diamine tetracetate, also known as edetates, with disodium edetate being a preferred ingredient. Other biocides that may be optionally included in the ophthalmic solution include thimerosal, phenylmercuric nitrate, chlorobutanol, and sorbic acid.

For most ophthalmic uses, it is desirable that the ophthalmic solution be isotonic. Conventionally, ophthalmic solutions are rendered isotonic by addition of suitable salts, for example, sodium chloride, potassium chloride, calcium chloride, magnesium chloride, and various nitrates, citrates, acetates, etc. The salts used to establish an isotonic condition should be monovalent, i.e., sodium chloride, potassium chloride, or mixtures thereof. Generally, the monovalent salts are added in an amount sufficient to give a freezing point depression or osmotic pressure equivalent to that provided by 0.5% to 1.5% sodium chloride, preferably 0.9% sodium chloride.

If desired, the solutions of the invention may be adjusted in pH by one or more of the acids or bases known for use in ophthalmic and/or otic solutions. The ophthalmic and/or otic solution may be maintained in an acidic, basic or neutral condition by use of buffers commonly employed in ophthalmic solutions. The use of suitable acids, bases, and buffering systems to establish a pH within the range of from about 3.0 to about 8.5 is well known and requires no further description. Typically, the pH of the ophthalmic and/or otic solutions described herein is between about 5.0 and 8.0, preferably between about 6.0 and about 7.5.

The following examples further illustrate various features of the invention but are not intended to in any way limit the scope of the invention which is defined in the appended claims.

EXAMPLE I

Seven ophthalmic solutions in accordance with the invention were prepared having the formulations set forth below in Table 1.

TABLE 1

| Formulation Ingredient | Formulation No. Percent w/v | | | | | | |
|---|---|---|---|---|---|---|---|
| | 1 | 2 | 3 | 4 | 5 | 6 | 7 |
| Bis-(2-pyridyl-1-oxide) disulfide magnesium sulfate | 0.5 | 0.1 | 0.5 | 0.1 | 0.1 | 0.1 | 0.1 |
| Arabinogalactan[1] | — | 0.2 | — | 0.2 | — | 0.1 | — |
| Benzalkonium chloride | — | — | 0.01 | 0.01 | 0.01 | 0.01 | 0.01 |
| Disodium ethylene diamine tetracetate | — | — | — | — | — | — | 0.05 |
| Sodium chloride | 0.8 | 0.8 | 0.7 | 0.8 | 0.8 | 0.8 | 0.7 |
| Potassium chloride | — | — | — | — | — | — | 0.1 |
| Water | qs | qs | qs | qs | qs | qs | qs |

[1]Commercially available under the tradename STRACTAN from Stein Hall Company

Each of the solutions were found to be effective for the treatment of eye inflammation.

EXAMPLE II

Five otic solutions in accordance with the present invention were prepared having the formulation set forth below in Table 2.

TABLE 2

| Formulation Ingredient | Formulation No. Percent w/v | | | | |
|---|---|---|---|---|---|
| | 1 | 2 | 3 | 4 | 5 |
| Bis-(2-pyridyl-1-oxide) sodium chloride | 0.1 | 0.1 | 0.1 | 0.5 | 1.0 |
| Polyethylene oxide | — | — | 0.1 | 0.1 | 0.5 |
| Polyvinyl alcohol | — | 2.0 | 2.0 | 2.0 | — |
| NaCl | 0.9 | 0.9 | 0.9 | 0.8 | 0.7 |
| Water | qs | qs | qs | qs | qs |

Each of the solutions were found to be effective for treatment of ear irritations.

EXAMPLE III

Solutions which could be utilized for ophthalmic or otic use were prepared as follows:

| Ingredient | Formulation No. | | |
|---|---|---|---|
| | 1 | 2 | 3 |
| Bis-(2-pyridyl-1-oxide) disulfide calcium acetate | 0.1% | 1.0% | 2.0% |
| Benzalkonium chloride | 0.01% | 0.01% | 0.01% |
| Bis-(2-pyridyl-1-oxide) sodium chloride | 0.05% | 0.05% | — |
| Sodium Chloride | 0.28% | 0.67% | 0.57% |
| Potassium Chloride | 0.075% | 0.12% | 0.12% |
| Calcium Chloride | 0.45% | — | — |
| Magnesium Chloride | 0.03% | — | — |
| Sodium Acetate | 0.30% | — | — |
| Sodium Citrate | 0.17% | — | — |
| Sodium Hydroxide | qs pH 7.0 | qs pH 7.0 | qs pH 7.0 |
| Hydroxypropylmethylcellulose | — | — | 0.3% |

-continued

| Ingredient | Formulation No. | | |
|---|---|---|---|
| | 1 | 2 | 3 |
| Purified Water | qs | qs | qs |

Each of the solutions were found to be effective for treatment of eye and ear irritations and inflammation.

I claim:

1. An ophthalmic and otic composition for treating eye and ear irritations and inflammation in warm blooded animals which comprises about 0.001 to about 5% by weight of the total composition of at least a compound selected from the group consisting of bis-(2-pyridyl-1-oxide) disulfide and the adducts of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2, together with a suitable isotonic pharmaceutical carrier.

2. The composition of claim 1, wherein M is magnesium, Y is sulfate and t is 1.

3. The composition of claim 1, wherein M is calcium, Y is chloride and t is 2.

4. The composition of claim 1, wherein M is calcium, magnesium or barium.

5. The composition of claim 1, wherein the formula is selected from the group consisting of $(C_5H_4NOS)_2CaCl_2$, $(C_5H_4NOS)_2MgSO_4$, $(C_5H_4NOS)_2SrCl_2$, $(C_5H_4NOS)_2SrBr_2$, $(C_5H_4NOS)_2Ca(NO_3)_2$ and $(C_5H_4NOS)_2Ba(ClO_3)_2$.

6. The composition of claim 1 which is an otic solution.

7. The composition of claim 1 which is an ophthalmic solution.

8. The composition of claim 7 including 0.001% to about 0.1% by weight of benzalkonium chloride.

9. The composition of claim 7 including a polysaccharide selected from the group consisting of dextrans having a molecular weight in the range of 10,000 to about 1,000,000 and arabinoglactans having a molecular weight in the range of 10,000 to about 250,000.

10. The composition of claim 1, wherein said adducts are water-soluble.

11. The composition of claim 1, wherein Y is selected from the group consisting of halides, sulfates, nitrates and acetates.

12. An ophthalmic composition for topically treating eye irritations and inflammation in warm blooded animals comprising an isotonic solution of 0.01 to about 2% by weight of said composition if bis-(2-pyridyl-1-oxide) disulfide magnesium sulfate and 0.004 to about 0.020% by weight of said composition of benzalkonium chloride.

13. The composition defined in claim 1, wherein the percentage by weight of bis-(2-pyridyl-1-oxide) disulfide magnesium sulfate is about 0.01% to about 2%.

14. A method of treating ear and eye irritations and inflammation in warm blooded animals which comprises administering to a warm blooded animal in need of such treatment a pharmaceutical isotonic solution containing an effective amount of a compound selected from the group consisting of bis-(2-pyridyl-1-oxide)

disulfide and an adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earch metals; Y is the anion of an inorganic or organic acid and t is either 1 or 2.

15. The method of claim 14 wherein said warm blooded animal is treated for conjunctivitis.

16. The method of claim 14 wherein said solution includes 0.001% to about 0.1% by weight of benzalkonium chloride.

17. A method for treating eye irritations and inflammation in warm blooded animals which comprises administering to a warm blooded animal in need of treatment, an ophthalmic isotonic solution containing 0.001 to about 5% by weight of the total solution of bis-(2-pyridyl-1-oxide) disulfide magnesium sulfate and 0.001% to about 0.1% by weight of the total solution of benzalkonium chloride.

18. The method defined in claim 17, wherein the percentage by weight of bis-(2-pyridyl-1-oxide) disulfide magnesium sulfate is about 0.01% to about 2%.

* * * * *